US010731687B2

(12) United States Patent
Ponzer et al.

(10) Patent No.: US 10,731,687 B2
(45) Date of Patent: Aug. 4, 2020

(54) INSTRUMENT COUPLING INTERFACES AND RELATED METHODS

(71) Applicant: Medos International Sarl, Le Locle (CH)

(72) Inventors: Rainer Ponzer, Oberdorf (CH); Philippe Lindenmann, Basel (CH)

(73) Assignee: Medos International Sarl, Le Locle (CH)

( * ) Notice: Subject to any disclaimer, the term of this patent is extended or adjusted under 35 U.S.C. 154(b) by 0 days.

(21) Appl. No.: 15/820,485

(22) Filed: Nov. 22, 2017

(65) Prior Publication Data

US 2019/0150901 A1    May 23, 2019

(51) Int. Cl.
*F16B 7/18* (2006.01)
*A61B 17/00* (2006.01)

(52) U.S. Cl.
CPC ...... *F16B 7/18* (2013.01); *A61B 2017/00477* (2013.01); *Y10T 403/1624* (2015.01); *Y10T 403/7069* (2015.01)

(58) Field of Classification Search
CPC .......... A61B 2017/00477; F16B 2/065; F16B 5/0088; F16B 5/02; F16B 5/025;
(Continued)

(56) References Cited

U.S. PATENT DOCUMENTS 5,993,101 A * 11/1999 Kohno ............... F16D 1/101
                                                       403/14
6,190,395 B1    2/2001 Williams
(Continued)

FOREIGN PATENT DOCUMENTS

EP    1 574 170 B1    4/2007
EP    2 793 728 A1    10/2014
(Continued)

OTHER PUBLICATIONS

International Search Report and Written Opinion for Application No. PCT/EP2018/082229, dated Feb. 26, 2019 (16 pages).

*Primary Examiner* — Josh Skroupa
(74) *Attorney, Agent, or Firm* — Nutter McClennen & Fish LLP

(57) ABSTRACT

Instruments can include coupling interfaces that can b used, for example, for coupling a surgical instrument to a navigation array or other component. An exemplary coupling can include a first coupling interface associated with a first object, such as a surgical instrument, and a second coupling interface associated with a second object, such as a navigation array. The coupling interfaces can be configured to ensure that, when mated, the first and second objects are disposed in a known position and orientation relative to one another and blocked from relative movement in all six degrees of freedom. The interfaces can have a geometry that is not overdetermined, minimizing or eliminating navigation inaccuracy associated with system tolerances. An exemplary coupling can include counterpart centering features for blocking X-axis translation and Y-axis translation, counterpart rotation stops for blocking Z-axis rotation, counterpart reference planes for blocking X-axis rotation, Y-axis rotation, and Z-axis translation in a first direction, and a locking element for blocking Z-axis translation in a second, opposite direction.

24 Claims, 10 Drawing Sheets

(58) Field of Classification Search
CPC .............. F16B 7/18; Y10T 403/1616; Y10T 403/1624; Y10T 403/5741; Y10T 403/5793; Y10T 403/589; Y10T 403/645; Y10T 403/7045; Y10T 403/7069; Y10T 403/7092
USPC .......... 403/13, 14, 306, 314, 320, 337, 364, 403/374.4, 380
See application file for complete search history.

(56) References Cited

U.S. PATENT DOCUMENTS

| | | | |
|---|---|---|---|
| 6,434,507 B1 | 8/2002 | Clayton et al. | |
| 6,556,857 B1 | 4/2003 | Estes et al. | |
| 6,746,172 B2 * | 6/2004 | Culpepper | F16M 7/00 403/13 |
| 6,932,823 B2 | 8/2005 | Grimm et al. | |
| 7,043,961 B2 | 5/2006 | Pandey et al. | |
| 7,153,297 B2 | 12/2006 | Peterson | |
| 7,153,308 B2 | 12/2006 | Peterson | |
| 7,166,114 B2 | 1/2007 | Moctezuma De La Barrera et al. | |
| 7,274,958 B2 | 9/2007 | Jutras et al. | |
| 7,289,227 B2 | 10/2007 | Smetak et al. | |
| 7,314,048 B2 | 1/2008 | Couture et al. | |
| 7,458,977 B2 | 12/2008 | McGinley et al. | |
| 7,559,265 B2 * | 7/2009 | Mizuno | B23B 31/1071 403/314 |
| 7,634,306 B2 | 12/2009 | Sarin et al. | |
| 7,668,584 B2 | 2/2010 | Jansen | |
| 7,688,998 B2 | 3/2010 | Tuma et al. | |
| 7,840,256 B2 | 11/2010 | Lakin et al. | |
| 7,862,568 B2 | 1/2011 | Vilsmeier et al. | |
| 7,873,400 B2 | 1/2011 | Moctezuma De La Barrera et al. | |
| 7,877,890 B2 | 2/2011 | Weber | |
| 7,993,353 B2 | 8/2011 | Roßner et al. | |
| 8,216,211 B2 | 7/2012 | Mathis et al. | |
| 8,271,066 B2 | 9/2012 | Sarin et al. | |
| 8,303,596 B2 | 11/2012 | Plaßky et al. | |
| 8,386,022 B2 | 2/2013 | Jutras et al. | |
| 8,419,750 B2 | 4/2013 | Kienzle, III et al. | |
| 8,509,878 B2 | 8/2013 | Pfeifer et al. | |
| 8,560,047 B2 | 10/2013 | Haider et al. | |
| 8,663,204 B2 | 3/2014 | Lechner et al. | |
| 8,688,196 B2 | 4/2014 | Whitmore, III et al. | |
| 8,715,296 B2 | 5/2014 | Plaßky et al. | |
| 8,734,432 B2 | 5/2014 | Tuma et al. | |
| 8,800,939 B2 | 8/2014 | Karsak et al. | |
| 8,821,511 B2 | 9/2014 | von Jako et al. | |
| 8,834,455 B2 | 9/2014 | Kleven | |
| 8,961,500 B2 | 2/2015 | Dicorleto et al. | |
| 8,961,536 B2 | 2/2015 | Nikou et al. | |
| RE45,484 E | 4/2015 | Foley et al. | |
| 9,005,211 B2 | 4/2015 | Brundobler et al. | |
| RE45,509 E | 5/2015 | Foley et al. | |
| 9,079,010 B2 | 7/2015 | Aho et al. | |
| 9,179,984 B2 | 11/2015 | Teichman et al. | |
| 9,232,985 B2 | 1/2016 | Jacobsen et al. | |
| 9,265,589 B2 | 2/2016 | Hartmann et al. | |
| 9,303,667 B2 * | 4/2016 | Morris | F16B 5/0664 |
| 9,393,039 B2 | 7/2016 | Lechner et al. | |
| 9,498,290 B2 | 11/2016 | Piferi et al. | |
| 9,539,060 B2 | 1/2017 | Lightcap et al. | |
| 9,541,113 B2 * | 1/2017 | Morris | F16B 19/02 |
| 9,649,160 B2 | 5/2017 | van der Walt et al. | |
| 9,737,287 B2 | 8/2017 | Gifford et al. | |
| 9,795,239 B1 | 10/2017 | Karasz et al. | |
| 9,827,052 B2 | 11/2017 | Fowler et al. | |
| 9,885,376 B1 * | 2/2018 | Meyer | F16B 7/18 |
| 10,004,562 B2 | 6/2018 | Kostrzewski et al. | |
| 10,028,789 B2 | 7/2018 | Quaid et al. | |
| 10,182,671 B2 * | 1/2019 | Firestone | A47F 8/00 |
| 10,288,097 B2 * | 5/2019 | Ayuzawa | F16B 5/02 |
| 2004/0068263 A1 | 4/2004 | Chouinard et al. | |
| 2004/0077940 A1 | 4/2004 | Kienzle et al. | |
| 2004/0152955 A1 | 8/2004 | McGinley et al. | |
| 2004/0171930 A1 | 9/2004 | Grimm et al. | |
| 2005/0049485 A1 | 3/2005 | Harmon et al. | |
| 2005/0109855 A1 | 5/2005 | McCombs | |
| 2005/0119639 A1 | 6/2005 | McCombs et al. | |
| 2005/0124988 A1 | 6/2005 | Terrill-Grisoni et al. | |
| 2005/0154296 A1 | 7/2005 | Lechner et al. | |
| 2005/0203539 A1 | 9/2005 | Grimm et al. | |
| 2006/0052691 A1 | 3/2006 | Hall et al. | |
| 2006/0161059 A1 | 7/2006 | Wilson | |
| 2007/0149977 A1 | 6/2007 | Heavener | |
| 2007/0225725 A1 | 9/2007 | Heavener et al. | |
| 2007/0287910 A1 | 12/2007 | Stallings et al. | |
| 2008/0045972 A1 | 2/2008 | Wagner et al. | |
| 2009/0180831 A1 * | 7/2009 | Kendall | F16B 5/025 403/408.1 |
| 2009/0306499 A1 | 12/2009 | Van Vorhis et al. | |
| 2010/0160932 A1 | 6/2010 | Gschwandtner et al. | |
| 2011/0263971 A1 | 10/2011 | Nikou et al. | |
| 2012/0004534 A1 | 1/2012 | Pfeifer et al. | |
| 2012/0232377 A1 | 9/2012 | Nottmeier | |
| 2013/0172907 A1 | 7/2013 | Harris | |
| 2013/0178745 A1 | 7/2013 | Kyle, Jr. et al. | |
| 2014/0257332 A1 | 9/2014 | Zastrozna | |
| 2014/0276007 A1 | 9/2014 | Sela et al. | |
| 2015/0093179 A1 * | 4/2015 | Morris | B62D 27/02 403/13 |
| 2015/0167717 A1 * | 6/2015 | Morris | F16B 5/0628 403/14 |
| 2015/0175217 A1 * | 6/2015 | Morris | B62D 27/023 403/14 |
| 2015/0182293 A1 | 7/2015 | Yang et al. | |
| 2015/0265769 A1 | 9/2015 | Bratbak et al. | |
| 2015/0297315 A1 | 10/2015 | Fowler et al. | |
| 2015/0305817 A1 | 10/2015 | Kostrzewski | |
| 2015/0375799 A1 * | 12/2015 | Morris | B60R 13/02 403/14 |
| 2016/0015374 A1 | 1/2016 | Gifford et al. | |
| 2016/0015474 A1 | 1/2016 | Dekel | |
| 2016/0030129 A1 | 2/2016 | Christian et al. | |
| 2017/0007353 A1 | 1/2017 | Fleig et al. | |
| 2017/0130754 A1 * | 5/2017 | Morrow | F16B 7/18 |
| 2018/0296365 A1 | 10/2018 | Nielsen et al. | |
| 2018/0344301 A1 | 12/2018 | Wehrli et al. | |
| 2019/0021795 A1 | 1/2019 | Crawford et al. | |

FOREIGN PATENT DOCUMENTS

| | | |
|---|---|---|
| WO | 2004030558 A1 | 4/2004 |
| WO | 2012103254 A2 | 8/2012 |
| WO | 2013115640 A1 | 8/2013 |
| WO | WO-2012103254 A3 * | 4/2014 |
| WO | 2015023853 A1 | 2/2015 |
| WO | WO-2015023853 A1 * | 2/2015 |
| WO | 2015162256 A1 | 10/2015 |
| WO | WO-2015162256 A1 * | 10/2015 |
| WO | 2016023599 A1 | 2/2016 |
| WO | 2016134266 A1 | 8/2016 |
| WO | WO-2016134266 A1 * | 8/2016 |
| WO | 2017200446 A1 | 11/2017 |

* cited by examiner

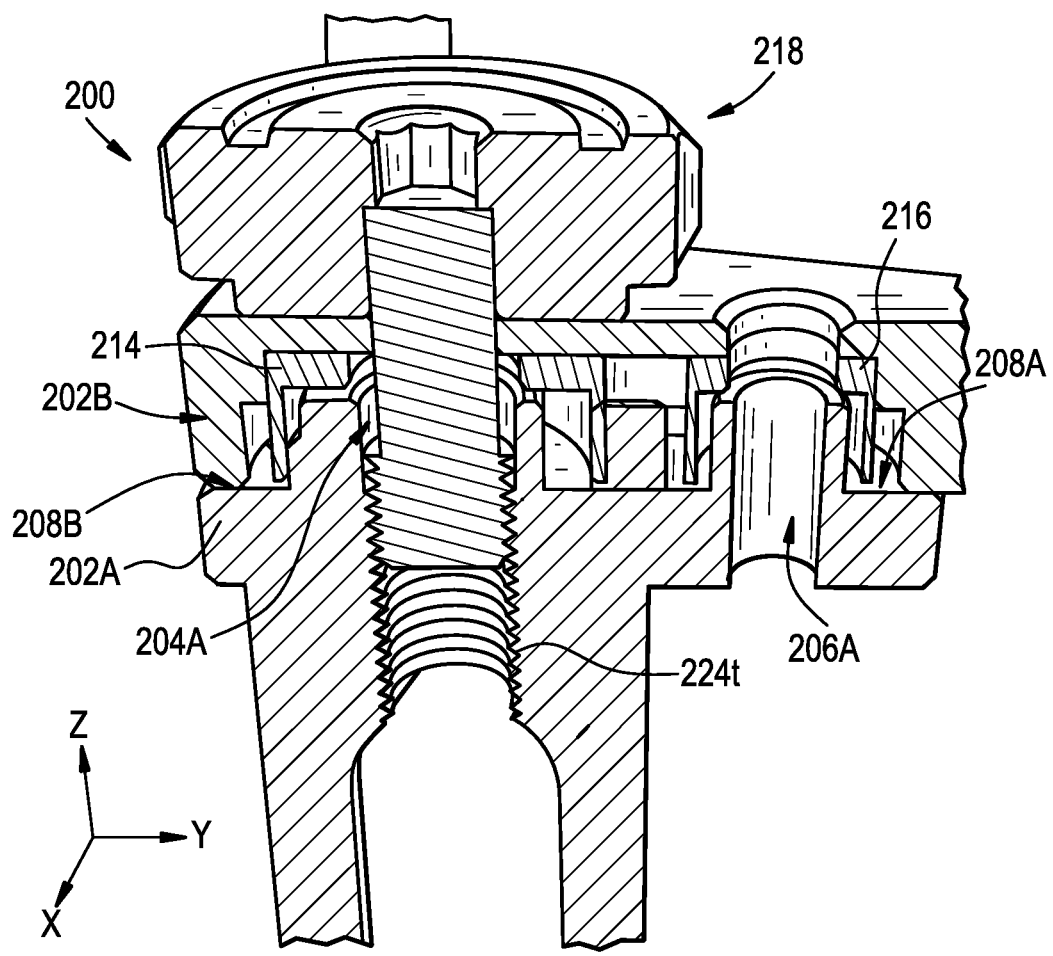

INSTRUMENT COUPLING INTERFACES AND RELATED METHODS

FIELD

Instrument coupling interfaces and related methods are disclosed herein, e.g., for coupling a surgical instrument to a navigation array or other component.

BACKGROUND

Navigation or tracking of instruments during surgical procedures has become increasingly popular. Surgical navigation can help surgeons avoid delicate neural or vascular structures when moving instruments within a patient. In spinal surgery, for example, a surgical navigation system can be used during disc removal, bone drilling, implant insertion, e.g., screw and/or cage insertion, and other steps of the surgery. Use of surgical navigation systems can also reduce the amount of X-ray exposure to which the patient and operating room staff are exposed.

A typical navigation system includes an array of markers attached to a surgical instrument, an imaging system that captures images of the surgical field, and a controller that detects the markers in the captured images and tracks movement of the markers within the surgical field. The controller associates a reference frame of the imaging system with a reference frame of the patient and, informed by a known geometry of the array and the instrument, determines how the instrument is being moved relative to the patient. Based on that determination, the controller provides navigation feedback to the surgeon. The arrays can have different types or geometries, which can vary based on the type of surgery and/or location within the patient that is being tracked.

The precision of the navigation system strongly depends on the design of the tracked instrument. Welding or integrally-forming the navigation array to the instrument can result in relatively high precision being achieved. Such solutions can be inconvenient, as the capability to decouple the array from the instrument or to couple the array to other instruments is absent. Further, arrangements having the navigation array integrally-formed with the instrument can require separate instruments for standard and navigation use, thereby raising costs for equipment.

A number of solutions have been developed to allow the navigation array to be interchangeably attached with one or more instruments. For example, these solutions can include interfaces that have dovetail or v-groove geometries to connect the navigation array to the instrument. These solutions can be geometrically overdetermined, which can make it difficult to consistently and repeatably attach the array and the instrument in a desired relative position and orientation. As a result, these solutions can allow for situations in which the navigation array is not defined in one or more degrees of freedom, which can undesirably reduce the precision of the navigation.

SUMMARY

Instrument coupling interfaces and related methods are disclosed herein, e.g., for coupling a surgical instrument to a navigation array or other component. An exemplary coupling can include a first coupling interface associated with a first object, such as a surgical instrument, and a second coupling interface associated with a second object, such as a navigation array. The coupling interfaces can be configured to ensure that, when mated, the first and second objects are disposed in a known position and orientation relative to one another and blocked from relative movement in all six degrees of freedom. The interfaces can have a geometry that is not overdetermined, minimizing or eliminating navigation inaccuracy associated with system tolerances. An exemplary coupling can include counterpart centering features for blocking X-axis translation and Y-axis translation, counterpart rotation stops for blocking Z-axis rotation, counterpart reference planes for blocking X-axis rotation, Y-axis rotation, and Z-axis translation in a first direction, and a locking element for blocking Z-axis translation in a second, opposite direction.

In some embodiments, a coupling for attaching first and second objects can include a first coupling interface associated with the first object, the first coupling interface having a first reference plane, a first centering feature, and a first rotation stop; and a second coupling interface associated with the second object, the second coupling interface having a second reference plane, a second centering feature, and a second rotation stop; wherein the first and second coupling interfaces are adapted to mate with one another such that the first reference plane contacts the second reference plane, the first centering feature contacts the second centering feature, and the first rotation stop contacts the second rotation stop.

The first centering feature can make cylindrical three point contact with the second centering feature. The first rotation stop can make cylindrical two point contact with the second rotation stop. The first and second reference planes, when mated, can lie in XY planes of a Cartesian system having an X-axis, a Y-axis, and a Z-axis. The first and second centering features can mate to block X-axis translation and Y-axis translation between the first and second objects. The first and second rotation stops can mate to block Z-axis rotation between the first and second objects. The first and second reference planes can mate to block Z-axis translation in a first direction, X-axis rotation, and Y-axis rotation between the first and second objects. The coupling can include a locking element that blocks Z-axis translation in a second direction between the first and second objects. The locking element can include at least one of: (i) friction between the centering features, (ii) friction between the rotation stops, (iii) a screw, and (iv) a clamp.

The first centering feature can include a centering protrusion. The second centering feature can include a centering recess. The centering protrusion can be press-fit into the centering recess. The centering recess can be configured to elastically deform upon insertion and removal of the centering protrusion therefrom. The centering protrusion can include three cylindrical outer contact surfaces configured to contact a cylindrical inner sidewall of the centering recess. The centering protrusion can include oblique lead-in surfaces disposed adjacent to the contact surfaces. The centering protrusion can have a triangular transverse cross-section. The centering recess can be recessed relative to the second reference plane.

The first rotation stop can include a rotation stop protrusion. The second rotation stop can include a rotation stop recess. The rotation stop protrusion can be press-fit into the rotation stop recess. The rotation stop recess can be configured to elastically deform upon insertion and removal of the rotation stop protrusion therefrom. The rotation stop protrusion can include two cylindrical outer contact surfaces configured to contact a cylindrical inner sidewall of the rotation stop recess. The rotation stop protrusion can include oblique lead-in surfaces disposed adjacent to the contact surfaces. The rotation stop protrusion can include two contact surfaces disposed along an arc centered on the first centering feature. The rotation stop protrusion can have a circular transverse cross-section with first and second lateral wings extending therefrom. The rotation stop recess can be recessed relative to the second reference plane.

The one of the first and second objects can be a surgical navigation array and the other of the first and second objects can be a surgical instrument. The coupling can include an alignment pin configured to prevent mating of the first and second coupling interfaces when the first and second coupling interfaces are not in a pre-determined alignment with one another. The coupling can include a locking screw configured to maintain the first and second coupling interfaces in a mated relationship. The locking screw can extend through the first and second centering features.

In some embodiments, a method of coupling a first object to a second object can include aligning a first coupling interface having a first planar contact surface with a first centering feature and a first rotation stop extending therefrom with a second coupling interface having a second planar contact surface with a second centering feature and a second rotation stop formed therein, the first and second planar contact surfaces lying in a plane defined by X- and Y-axes and having a Z-axis extending perpendicularly therefrom; and advancing the second coupling interface with respect to the first coupling interface such that the first centering feature is received within the second centering feature, the first rotation stop is received within the second rotation stop, and the first planar contact surface is in contact with the second planar contact surface.

The first centering feature can make cylindrical three point contact with the second centering feature. The first rotation stop can make cylindrical two point contact with the second rotation stop. The method can include elastically deforming the second centering feature and the second rotation stop as the first centering feature and the first rotation stop are inserted therein. The method can include actuating a locking element to retain the first and second coupling interfaces in a mated relationship. The method can include actuating a locking element to urge the first and second coupling interfaces towards one another or to urge the first and second coupling interfaces away from one another.

BRIEF DESCRIPTION OF THE DRAWINGS

The following detailed description is provided with the accompanying drawings, in which:

FIG. 4 is a sectional perspective view of the coupling of FIG. 2 after assembly;

DETAILED DESCRIPTION

Instrument coupling interfaces and related methods are disclosed herein, e.g., for coupling a surgical instrument to a navigation array or other component. An exemplary coupling can include a first coupling interface associated with a first object, such as a surgical instrument, and a second coupling interface associated with a second object, such as a navigation array. The coupling interfaces can be configured to ensure that, when mated, the first and second objects are disposed in a known position and orientation relative to one another and blocked from relative movement in all six degrees of freedom. The interfaces can have a geometry that is not overdetermined, minimizing or eliminating navigation inaccuracy associated with system tolerances. An exemplary coupling can include counterpart centering features for blocking X-axis translation and Y-axis translation, counterpart rotation stops for blocking Z-axis rotation, counterpart reference planes for blocking X-axis rotation, Y-axis rotation, and Z-axis translation in a first direction, and a locking element for blocking Z-axis translation in a second, opposite direction.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments. The features illustrated or described in connection with one exemplary embodiment may be combined with the features of other embodiments.

Prior Art Coupling

Figure 1A:
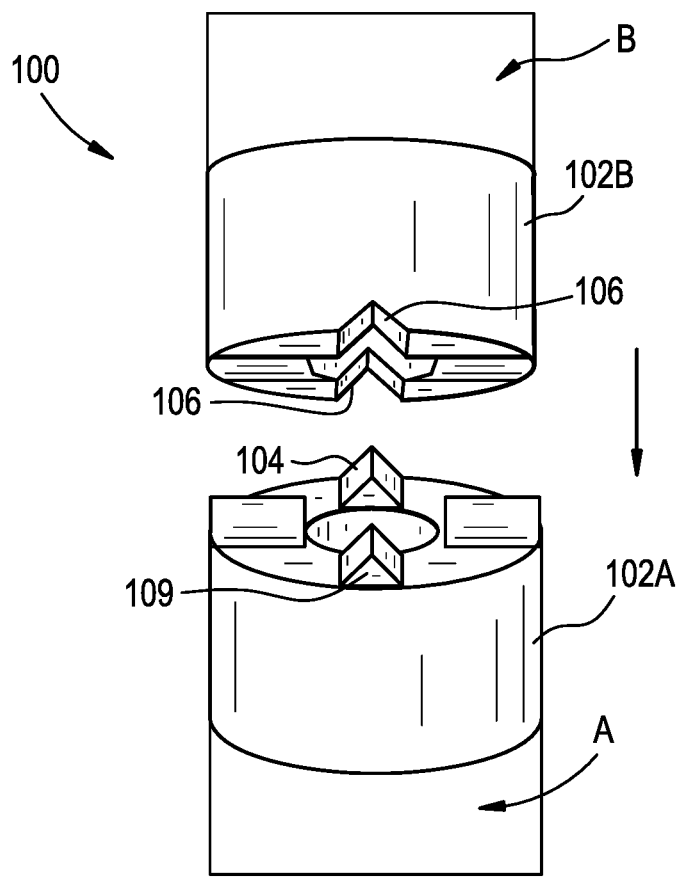
FIG. 1A is an exploded perspective view of a prior art coupling.
Figure 1B:
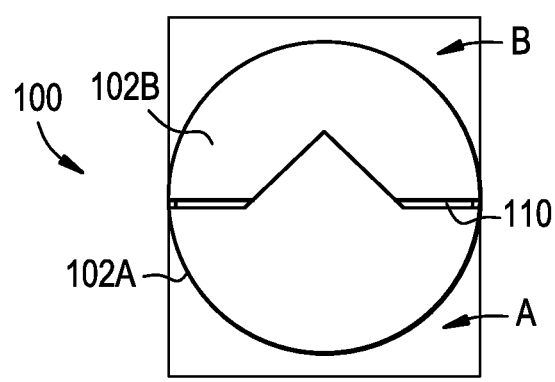
FIG. 1B is a detail side view of the prior art coupling of FIG. 1A.

FIGS. 1A-1B illustrate a prior art coupling 100 for attaching two objects. The coupling 100 includes a first coupling interface 102A associated with a first object A and a second coupling interface 102B associated with a second object B. The first coupling interface 102A includes four V-shaped protrusions 104 that are received within four corresponding V-shaped recesses 106 of the second coupling interface 102B when the coupling interfaces 102A, 102B are mated. The illustrated coupling 100 has an overdetermined geometry, in that there are more contact points or surfaces than necessary to constrain the objects A, B in the desired degrees of freedom (the illustrated coupling 100 includes at least eight possible contact surfaces between the interfaces 102A, 102B). The number of protrusions and corresponding grooves may be equal or greater than three. Such a geometry can introduce error when tolerances are suboptimal. For example, depending on tolerances, not all of the eight contact surfaces may actually be in contact with each other, which can allow some degree of "play" between the objects A, B, e.g., due to a gap 110 being formed therebetween as shown in FIG. 1B. As another example, different objects which are intended to have identical coupling interfaces may actually have coupling interfaces that vary slightly from one object to the next. In such cases, when mated to a first object A, different second objects may contact different ones of the eight surfaces, such that it is not possible to obtain a repeatable known position and orientation between the two mated objects. While a V-groove geometry is shown, dovetail and other type connections can also be overdetermined and suffer from similar inaccuracies. When these couplings are used, the tolerances must be tightly controlled, which can increase manufacturing cost and decrease manufacturing yield, or a certain level of inaccuracy must be accepted. Cone or V-shaped surfaces can be very sensitive to tolerances which can lead to varying gap size when the mating surfaces are brought together.

Instrument Coupling Interfaces and Related Methods

Figure 2:
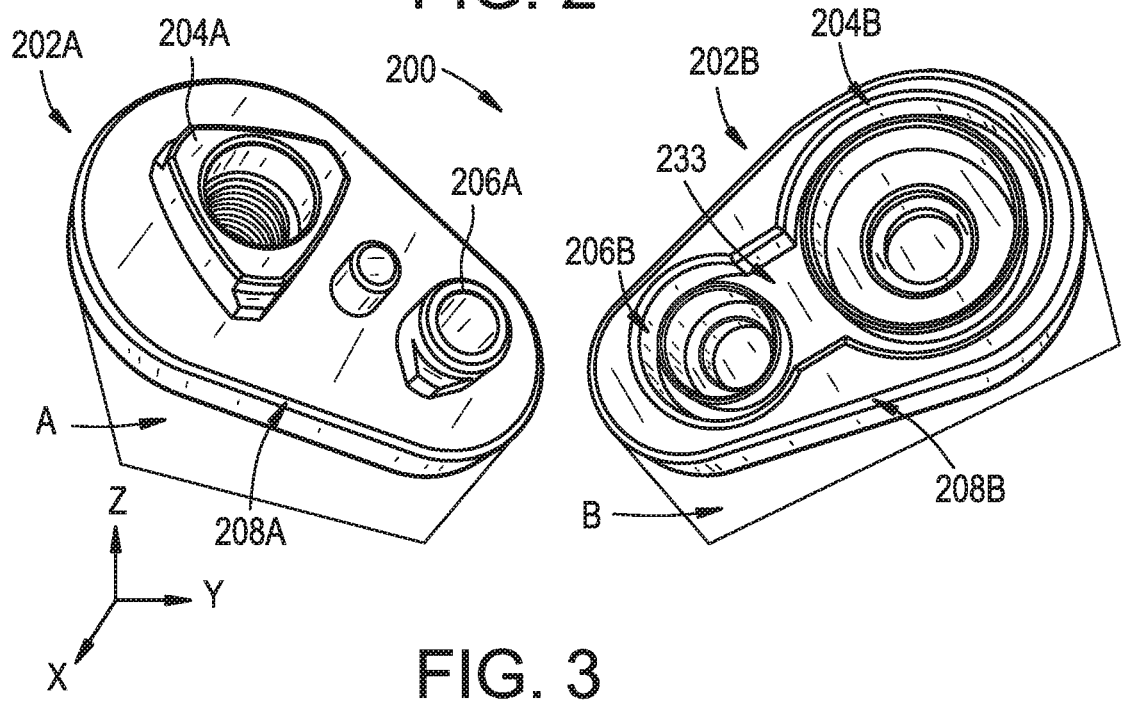
FIG. 2 is a perspective view of first and second coupling interfaces of an exemplary coupling.
Figure 3:
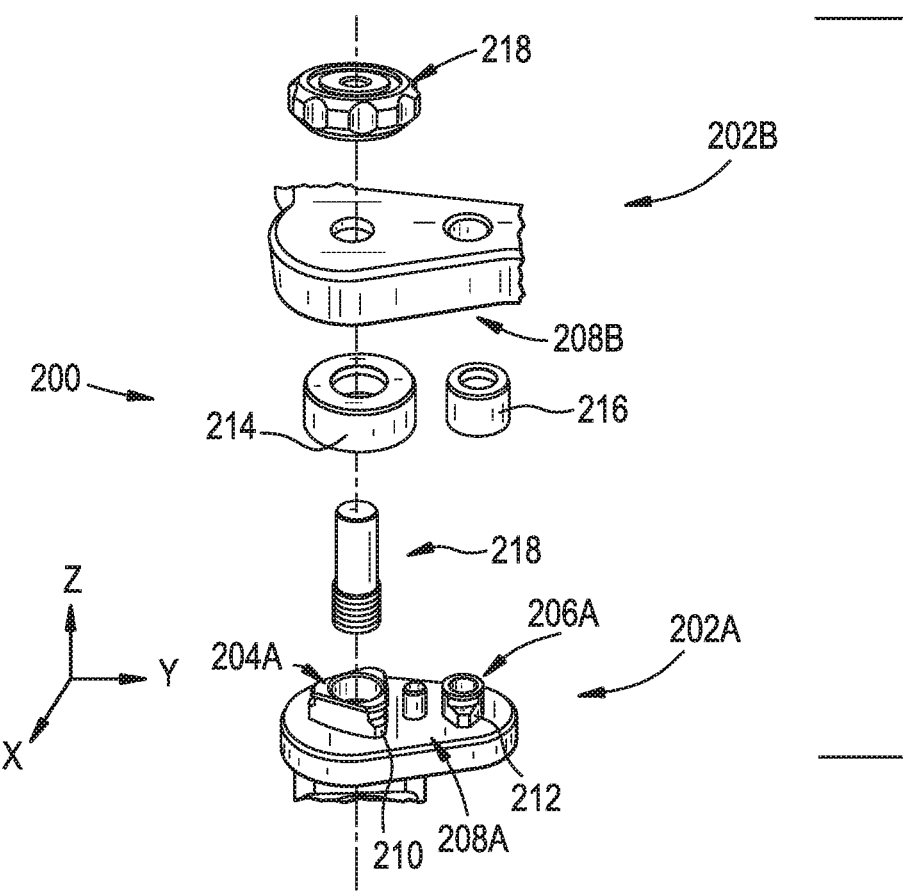
FIG. 3 is an exploded perspective view of the coupling of FIG. 2.

FIGS. 2-4 illustrate an exemplary embodiment of a coupling 200 that can be used to connect a first object A to a second object B. For example, the coupling 200 can connect a surgical instrument to a navigation array. The coupling 200 can achieve consistent relative positioning of the first and second objects A, B with fewer contact points than traditional couplings, and can be less prone to error introduced by system tolerances. As shown, the coupling 200 can include a first coupling interface 202A and a second coupling interface 202B. Each of the first and second coupling interfaces 202A, 202B can be formed on, or attached to, a respective one of the first and second objects A, B. The first and second coupling interfaces 202A, 202B can engage one another to lock all degrees of freedom between the objects A, B and to consistently and repeatably attach the objects A, B in a known relative position and orientation. The first and second coupling interfaces 202A, 202B can be formed integrally with the first and second objects A, B, or can be separate components that are welded, threaded, glued, or otherwise associated with or attached to the first and second objects A, B. Various aspects of the first and second coupling interfaces 202A, 202B can be described in relation to X-, Y-, and Z-axes of a Cartesian coordinate system, as shown in FIGS. 2-4.

The first coupling interface 202A can include a centering feature 204A. The centering feature 204A can mate with a counterpart centering feature of the second coupling interface 202B to block relative translation between the objects in the XY plane. The centering feature 204A can include a first protrusion having one or more engagement features thereon. For example, as shown, the engagement features can include three contact surfaces 210 configured to contact a corresponding centering feature of the second coupling interface 202B.

The first coupling interface 202A can include a rotation stop 206A. The rotation stop 206A can mate with a counterpart rotation stop of the second coupling interface 202B to block rotational movement of the first and second objects A, B relative to one another about the Z-axis. The rotation stop 206A can include a second protrusion having one or more engagement features thereon. For example, as shown, the engagement features can include two contact surfaces 212 configured to contact a corresponding rotation stop of the second coupling interface 202B.

The first coupling interface 202A can include a planar reference surface or reference plane 208A. The reference plane 208A can mate with a counterpart reference plane of the second coupling interface 202B to block rotational movement of the first and second objects A, B relative to one another about the X- and Y-axes and to block relative translation between the objects A, B in a first direction along the Z-axis. As discussed further below, a locking element can block relative translation between the objects A, B in a second, opposite direction along the Z-axis. The reference plane 208A can include a planar contact surface. In some embodiments, the first and second protrusions of the centering feature 204A and the rotation stop 206A can extend from the planar contact surface. In other arrangements, the planar contact surface can be offset, or located remotely, from the centering feature 204A and/or the rotation stop 206A. As shown, the X- and Y-axes can be parallel to the reference plane 208A, with the Z-axis being perpendicular to the reference plane 208A.

The second coupling interface 202B can include a centering feature 204B. The centering feature 204B can include a first recess having one or more engagement features therein. For example, as shown, the engagement features can include a cylindrical sidewall of the second object B or of a first bushing 214 mounted thereto.

The second coupling interface 202B can include a rotation stop 206B. The rotation stop 206B can include a second recess having one or more engagement features therein. For example, as shown, the engagement features can include a cylindrical sidewall of the second object B or of a second bushing 216 mounted thereto.

The second coupling interface 202B can include a reference plane 208B. For example, the reference plane 208B can include a planar contact surface from which the first and second recesses extend. As shown, the X- and Y-axes can be parallel to the reference plane 208B, with the Z-axis being perpendicular to the reference plane 208B.

In use, the first and second coupling interfaces 202A, 202B can be coupled to one another to lock all degrees of freedom between the first and second objects A, B and to position the first and second objects A, B in a predetermined relative position and orientation. For example, as shown in FIG. 4, the reference plane 208A of the first coupling interface 202A can contact the reference plane 208B of the second coupling interface 202B such that the surfaces 208A, 208B are parallel to one another. Engagement between the surfaces 208A, 208B can block Z-axis translation (in a first direction), X-axis rotation, and Y-axis rotation between the first and second objects A, B. The centering feature 204A of the first coupling interface 202A can be received within the corresponding centering feature 204B of the second coupling interface 202B to block X-axis translation and Y-axis translation between the first and second objects A, B. The rotation stop 206A of the first coupling interface 202A can be received within the corresponding rotation stop 206B of the second coupling interface 202B to block Z-axis rotation between the first and second objects A, B. Z-axis translation in a second direction opposite the first direction can be blocked by a locking element 218, as described below. The locking element 218 can extend through the coupling 200. The locking element 218 can extend through the centering feature 204A. The locking element 218 can extend through the rotation stop 206A. The locking element 218 can be disposed between the centering feature 204A and the rotation stop 206A. The locking element 218 can clamp to an outer rim of the first and second objects A, B, e.g., adjacent the reference planes 208A, 208B, or to other surfaces of the first and second objects A, B. The locking element 218 can be tightened, applied, or otherwise actuated to maintain the coupling interfaces 202A, 202B in engagement with one another.

In addition to blocking all degrees of freedom between the first and second objects A, B, the coupling interfaces 202A, 202B can function to automatically bring the first and second objects into a predetermined alignment when the coupling interfaces are mated. In other words, the coupling interfaces 202A, 202B can ensure that the first and second objects A, B are consistently and repeatably placed in a known position and orientation relative to one another when the coupling interfaces 202A, 202B are mated.

The coupling 200 can employ a minimum number of contact points to achieve the desired positioning of the objects A, B. For example, the centering features 204A, 204B can contact one another at exactly three points, the minimum needed to center a post within a recess. As another example, the rotation stops 206A, 206B can contact one another at exactly two points, the minimum needed to prevent clockwise and counterclockwise rotation about a central axis. The coupling 200 can be configured to lock all degrees of freedom between the objects A, B and can guarantee a known and consistent orientation between the two objects, regardless of tolerances. It will be appreciated that one or more of the counterpart mating features can be interchanged between the first and second interfaces 202A, 202B. For example, while the illustrated arrangement includes a first interface 202A with two male features 204A, 206A and a second interface 202B with two female features 204B, 206B, other arrangements can include one male and one female feature on each interface, can include a greater or lesser number of features, etc. The coupling 200 can provide a self-centering, toggle-free connection between two objects. The coupling 200 can provide a fully-constrained connection between two objects.

Figure 5A:
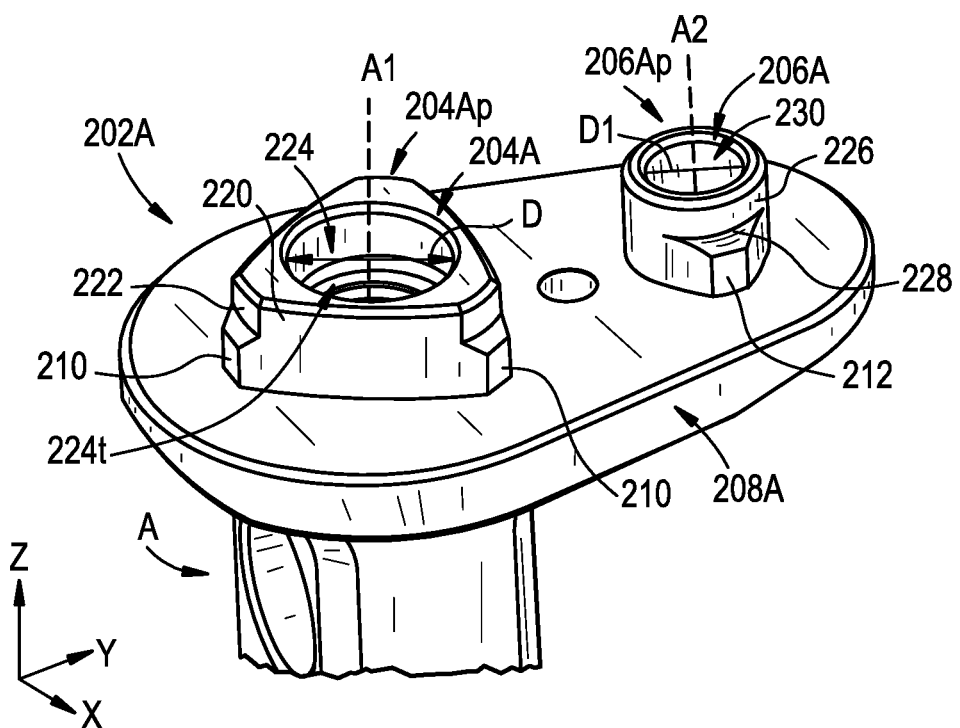
FIG. 5A is a perspective view of the first coupling interface of FIG. 2.
Figure 5B:
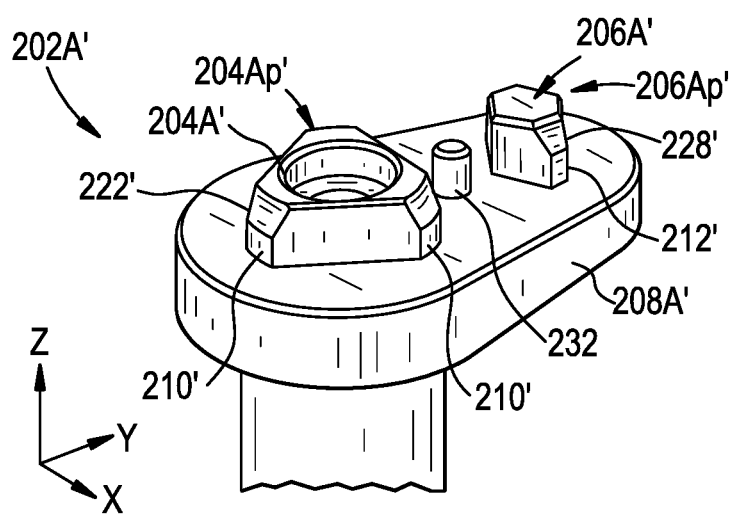
FIG. 5B is a perspective view of another first coupling interface that can be used with the coupling of FIG. 2.

The first coupling interface 202A is shown in greater detail in FIGS. 5A-5B. The centering feature 204A can extend from the reference plane 208A in the Z direction, as shown. The centering feature 204A can form a protrusion that is defined by a sidewall 220 and that includes a central longitudinal axis A1.

The centering feature 204A can include three contact surfaces 210. The contact surfaces 210 can engage a portion of the counterpart centering feature 204B of the second coupling interface 202B. The contact surfaces 210 can be spaced along the perimeter of the sidewall 220. The contact surfaces 210 can be formed on lateral extensions of the centering feature 204A, as three discrete protrusions, or in various other ways.

The contact surfaces 210 can define sections of a cylinder centered on the central longitudinal axis A1. As compared to sharp edges or line contact, cylindrical contact surfaces 210 can wear better and can provide a larger contact area during deformation of the counterpart centering feature 204B that may occur as a result coupling. A larger contact area can allow for a more secure fit to be formed at the coupling 200 between the first and second coupling interfaces 202A, 202B. In some embodiments, the contact surfaces 210 can be sharp edges.

The contact surfaces 210 can be oriented substantially perpendicular to the reference plane 208A, though, in some embodiments, one or more of the contact surfaces 210 can be obliquely angled relative to the reference plane 208A. Three contact surfaces 210 is the minimum number of contact points required to center the centering feature 204A in the XY plane within a cylindrical counterpart coupling interface. Having the minimum number of contact surfaces can ensure that the geometry of the centering feature 204A is not overdetermined at the coupling 200.

The contact surfaces 210 can be spaced uniformly along the sidewall 220, though, in some embodiments, distances between the contact surfaces 210 can differ. As shown in FIG. 5A, the contact surfaces 210 can be spaced about 120 degrees apart from one another around the perimeter of the centering feature 204A.

While three contact surfaces are shown, the centering feature 204A can alternatively have one, two, or four or more contact surfaces 210 that can engage with a corresponding centering feature 204B.

The centering feature 204A can include one or more lead-in surfaces 222. The lead-in surfaces 222 can be formed proximal to the contact surfaces 210 to facilitate coupling between centering features 204A, 204B. The lead-in surfaces 222 can be aligned with the contact surfaces 210 to allow the centering feature 204B of the second coupling interface 202B to slide along the centering feature 204A of the first coupling interface 202A during coupling prior to engaging with the contact surfaces 210.

The lead-in surfaces 222 can be chamfered, curved, stepped, or tapered to form a lead-in surface proximal to the contact surfaces 210. As shown in FIG. 5A, the lead-in surfaces 222 can extend radially-outward in a proximal-to-distal or top-to-bottom direction. Each lead-in surface 222 can extend at an oblique angle from the sidewall 220 to allow the centering feature 204B of the second coupling interface 202B to slide relative thereto as it travels distally for coupling. The lead-in surfaces 222 can protect the contact surfaces 210 from damage during handling and/or use. Sliding along the lead-in surfaces 222 prior to abutting the contact surfaces 210 can allow the centering feature 204B to gradually couple to the centering feature 204A as it travels distally. The lead-in surfaces 222 can also minimize damage to the contact surfaces 210 during coupling by absorbing forces caused by jarring or relative motion of the coupling 200. Damage or excessive wear to the contact surfaces 210 can compromise navigation accuracy.

The sidewall 220 can circumscribe a bore 224 formed in the centering feature 204A. The bore 224 can extend along the central longitudinal axis A1 from a proximal surface 204Ap of the centering feature 204A towards the planar contact surface 208A. The bore 224 can define a diameter D. The bore 224 can be configured to receive the locking element 218 therein. The bore 224 can include a threaded interior surface 224t or other mating features for interacting with the locking element 218.

As shown, the sidewall 220 of the centering feature 204A can extend between contact surfaces 210. The sidewall 220 can have a generally triangular shape as shown, though the sidewall can be rectangular, cylindrical, round, oval, and so forth. In some embodiments, the sidewall 220 can be set back or can form a concave shape between the contact surfaces 210 to provide a relief area for deformation of the centering feature 204B of the second coupling interface 202B.

The rotation stop 206A can extend from the reference plane 208A in the Z direction, as shown. The rotation stop 206A can form a protrusion that is defined by a sidewall 226 and that includes a central longitudinal axis A2. The central longitudinal axis A2 can be parallel or substantially parallel to the central longitudinal axis A1. The axes A1, A2 can be obliquely angled relative to one another.

The rotation stop 206A can include two contact surfaces 212. The contact surfaces 212 can engage a portion of the counterpart rotation stop 206B of the second coupling interface 202B. The contact surfaces 212 can be spaced along the perimeter of the sidewall 226. The contact surfaces 212 can be formed on lateral extensions of the rotation stop 206A, as two discrete protrusions, or in various other ways.

The contact surfaces 212 can be oriented along an arc centered on the central longitudinal axis A1 of the centering feature 204A. The contact surfaces 212 can engage a portion of the corresponding rotation stop 206B, as discussed further below, to prevent rotation of the second coupling interface 202B about the Z-axis, e.g., around the central longitudinal axis A1 of centering feature 204A. It will be appreciated that one of the contact surfaces 212 can prevent clockwise rotation of the second coupling interface 202B and a second contact surface 212 can prevent counterclockwise rotation of the second coupling interface 202B.

The contact surfaces 212 can define sections of a cylinder centered on the central longitudinal axis A2. As compared to sharp edges or line contact, cylindrical contact surfaces 212 can wear better and provide a larger contact area during deformation of the counterpart rotation stop 206B that may occur as a result of coupling. A larger contact area can allow a more secure fit to be formed at the coupling 200 between the first and second coupling interfaces 202A, 202B. In some embodiments, the contact surfaces 212 can be sharp edges.

The contact surfaces 212 can be oriented substantially perpendicular to the reference plane 208A, though, in some embodiments, one or more of the contact surfaces 212 can be obliquely angled relative to the reference plane. Two contact surfaces 212 is the minimum number of contact points required to keep the second coupling interface 202B from rotating about the central longitudinal axis A1. Additional contact surfaces can be used, but two are all that is needed to block rotation about the Z-axis. Having the minimum number of contact surfaces 212 can advantageously prevent tolerance in the offset between the centering feature 204B and the rotation stop 206B from contributing error to the system.

The contact surfaces 212 can be spaced uniformly along the sidewall 226, though, in some embodiments, distances between the contact surfaces 212 can differ. As shown in FIG. 5A, the contact surfaces 212 can be spaced about 180 degrees apart from one another around the perimeter of the rotation stop 206A. While two contact surfaces are shown, the rotation stop can alternatively have one or three or more contact surfaces 212 that can engage with a corresponding rotation stop 206B.

The rotation stop 206A can include one or more lead-in surfaces 228. The lead-in surfaces 228 can be formed proximal to the contact surfaces 212 to facilitate coupling between the rotation stops 206A, 206B. The lead-in surfaces 228 can be aligned with the contact surfaces 210 to allow the rotation stop 206B of the second coupling interface 202B to slide along the rotation stop 206A of the first coupling interface 202A during coupling prior to engaging with the contact surfaces 212.

The lead-in surfaces 228 can be chamfered, curved, stepped, or tapered to form a lead-in surface proximal to the contact surfaces 212. As shown in FIG. 5A, the lead-in surfaces 228 can extend radially-outward in a proximal-to-distal or top-to-bottom direction. Each lead-in surface 228 can extend at an oblique angle from the sidewall 226 to allow the rotation stop 206B of the second coupling interface 202B to slide relative thereto as it travels distally for coupling. The lead-in surfaces 228 can protect the contact surfaces 212 from damage during handling and/or use. Sliding along the lead-in surfaces 228 prior to abutting the contact surfaces 212 can allow the rotation stop 206B to gradually couple to the rotation stop 206A as it travels distally. The lead-in surfaces 228 can also minimize damage to the contact surfaces 212 during coupling by absorbing forces caused by jarring or relative motion of the coupling 200. Damage or excessive wear to the contact surfaces 212 can compromise navigation accuracy.

The sidewall 226 can circumscribe a bore 230 formed in the rotation stop 206A. The bore 230 can extend along the central longitudinal axis A2 from a proximal surface 206Ap of the rotation stop 206A towards the planar contact surface 208A. The bore 230 can define a diameter D1. The bore 230 can be configured to receive the locking element 218 therein. The bore 230 can include a threaded interior surface (not shown) or other mating features for interacting with the locking element 218. In some embodiments, as described with regards to FIG. 5B below, the bore 230 can be omitted from the rotation stop 206B.

As shown, the sidewall 226 of the rotation stop 206A can extend between the contact surfaces 212. The sidewall 226 can have a generally cylindrical shape as shown, though the sidewall 226 can be rectangular, round, triangular, oval, and so forth. In some embodiments, the sidewall 226 can be set back or can form a concave shape between the contact surfaces 212 to provide a relief area for deformation of the rotation stop 206B of the second coupling interface 202B.

The reference plane 208A can be formed in or on an exterior surface of the first object A. The centering feature 204A and the rotation stop 206A can protrude from the reference plane 208A. The planar contact surface 208A can lie in an XY plane, as shown. The reference plane 208A can prevent relative translation in the Z-axis, as well as rotation about the X- and Y-axes, when placed in contact with the second reference plane 208B.

FIG. 5B illustrates an alternate embodiment of the first coupling interface 202A'. The first coupling interface 202A' can include a centering feature 204A' and a rotation stop 206A' that protrude from a reference plane 208A'. The lead-in surfaces 222', 228' of the centering feature 204A' and the rotation stop 206A' can have angles of varying steepness. As shown, the lead-in surfaces 222', 228' can extend from proximal ends 204Ap', 206Ap' of the protrusions to the contact surfaces thereof. The steepness of the lead-in surfaces 222', 228' can impact how gradually the contact surfaces 210', 212' are engaged during coupling 200. The greater the angle the less gradually the contact surfaces 212' can be engaged.

The first coupling interface 202A' can include an alignment key 232. As shown in FIG. 5B, the alignment key 232 can be a guide cylinder or pin that protrudes or extends from the reference plane 208A'. It will be appreciated the alignment key 232 can extend a smaller distance than the centering feature 204A' and the rotation stop 206A', as shown, or a greater distance than either one of the centering feature 204A' or the rotation stop 206A', or both. The alignment key 232 can extend through the centering feature 204A'. The alignment key 232 can extend through the rotation stop 206A'. The alignment key 232 can be disposed between the centering feature 204A' and the rotation stop 206A'. The alignment key 232 can be disposed on other surfaces of the first and second coupling interfaces 202A', 202B or the first and second objects A, B.

The alignment key 232 can ensure that the first and second coupling interfaces 202A', 202B can only be attached in a single orientation, thereby preventing misaligned attachment therebetween. In the illustrated embodiment, the coupling 200 between the first and second interfaces 202A', 202B can occur in a single orientation, with other orientations considered to be misaligned. During proper alignment of the first and second coupling interfaces 202A', 202B, at least a portion of the alignment key 232 can be received within a corresponding feature or recess 233 in the second coupling interface 202B when the protrusions of the first coupling interface 202A' are coupled to the corresponding recesses of the second coupling interface 202B. During improper alignment of the first and second coupling interfaces 202A', 202B, the alignment key 232 can abut a non-recessed portion of the second coupling interface 202B, which can prevent coupling until the interfaces are properly aligned.

It will be appreciated that the alignment key 232 can be located between the centering feature 204A' and the rotation stop 206A', as shown, though, in some embodiments, the alignment key 232 can be located at an end of the reference plane 208A' such that the centering feature is located between the alignment key and the rotation stop, or the rotation stop is located between the alignment key and the centering feature. While not shown, the coupling interface 202A shown in FIG. 5A can include an alignment key of the type described herein.

Figure 5C:
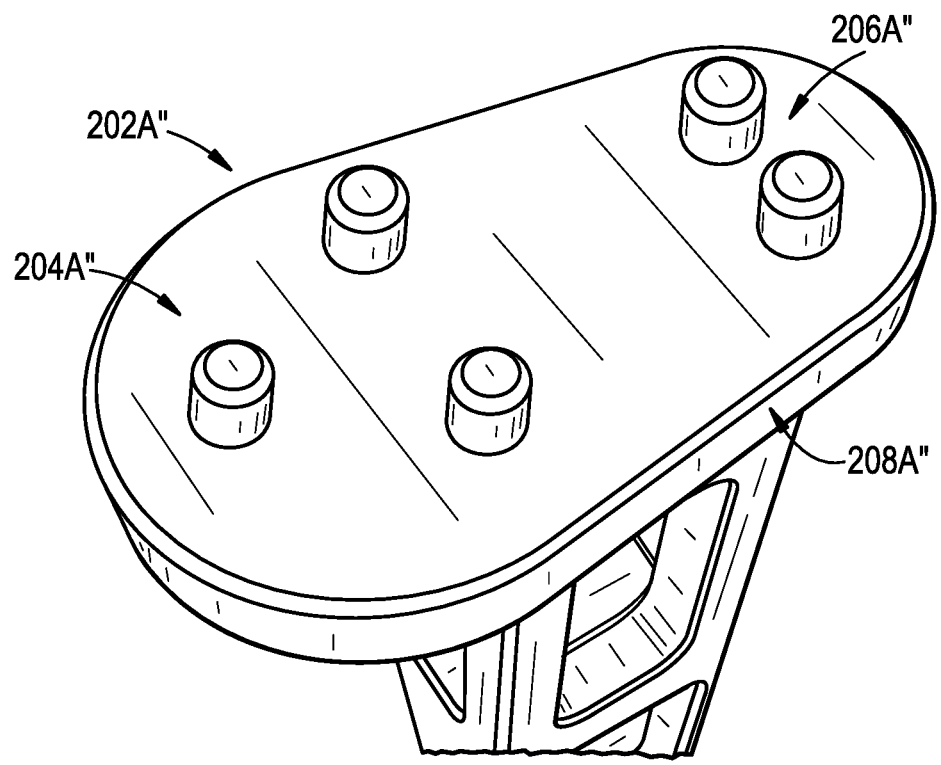
FIG. 5C is a perspective view of another first coupling interface that can be used with the coupling of FIG. 2.

FIG. 5C illustrates an alternate embodiment of the first coupling interface 202A". The first coupling interface 202A" can include a centering feature 204A" and a rotation stop 206A", one or both of which can be defined by a plurality of pins. As shown, the centering feature 204A" can include three pins arranged in a triangle pattern that protrude from the reference plane 208A". The rotation stop 206A" can include two pins arranged in a line that protrude from the reference plane 208A". The pins can be located on the first coupling interface 202A" to function in the same manner as the contact surfaces 210, 212 described above.

Figure 6A:
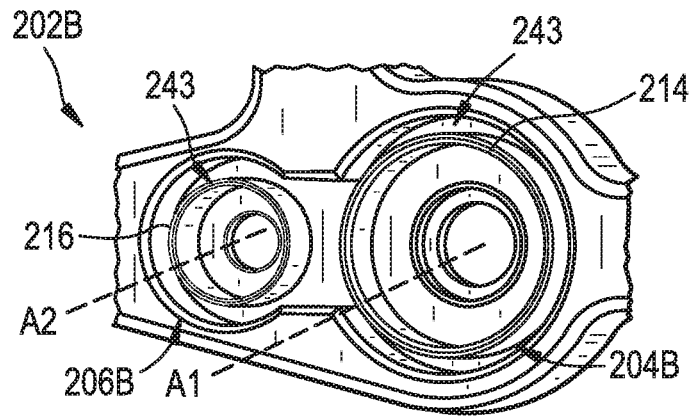
FIG. 6A is a perspective view of the second coupling interface of FIG. 2.
Figure 6B:
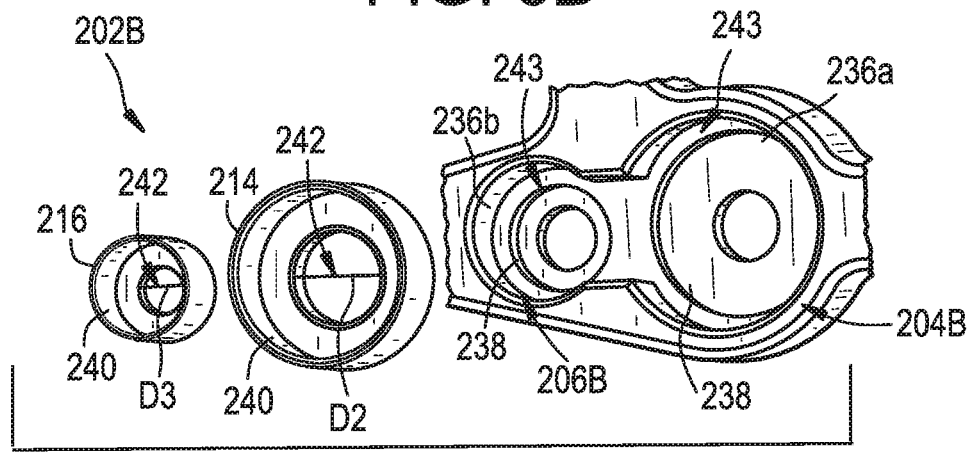
FIG. 6B is an exploded perspective view of the second coupling interface of FIG. 6A.

The second coupling interface 202B is shown in greater detail in FIGS. 6A-6B. As noted above, the second coupling interface 202B can include a planar contact surface 208B having a centering feature 204B and a rotation stop 206B extending in the Z direction therefrom, e.g., in a proximally-recessed manner as shown. Each of the centering feature 204B and the rotation stop 206B can include a recess 236a, 236b in the planar contact surface 208B configured to receive respective cylindrical bushings 214, 216 therein. The bushings 214, 216 can engage the contact surfaces 210, 212 of the first coupling interface 202A to facilitate coupling. As shown, each recess 236a, 236b can include an indent 238 configured to receive the respective bushing 214, 216 therein. In other arrangements, one or both bushings 214, 216 can be omitted such that the centering feature 204A and rotation stop 206A of the first mating interface 202A directly engage the recesses 236a, 236b.

Each bushing 214, 216 can extend distally from a corresponding recess 236a, 236b in the second coupling interface 202B. Each bushing 214, 216 can be formed integrally with the second coupling interface 202B, or can be a separate cup that is press-fit or attached to the recesses of the second coupling interface, as shown in FIG. 6B. The bushings 214, 216 can be manufactured from a thin and/or flexible material, e.g., stainless steel, nickel, aluminum, etc., to allow for deformation during assembly and disassembly.

The bushings 214, 216 can include a generally cylindrically-shaped body defined by a sidewall 240 having a central opening 242. The opening 242 can extend along the axes A1, A2 of the centering feature 204A and the rotation stop 206A, respectively, when the first and second coupling interfaces 202A, 202B are mated. The opening 242 of each bushing 214, 216 can be configured to receive the centering feature 204A and/or the rotation stop 206A of the first coupling interface 202A therethrough.

The bushings 214, 216 can be sized and shaped to correspond to the recess 236a, 236b that is configured to receive the bushing. For example, the bushing 214 of the centering feature 204B can have a diameter D2 and the bushing 216 of the rotation stop 206B can have a diameter D3. The bushing 214 of the centering feature 204B can be configured such that it cannot be received in the recess 236b of the rotation stop 206B. Likewise, the bushing 216 of the rotation stop 206B can be configured such that it cannot be received in the recess 236a of the centering feature 204B so as to sit within the indent 238. The bushings 214, 216 can be mounted flush or sub-flush relative to the planar contact surface 208B, which can help prevent the bushings 214, 216 from being damaged during handling or use.

It will be appreciated that the diameter D2 being different from the diameter D3 can ensure that the coupling between the first and second interfaces 202A, 202B occurs only in a single orientation. For example, the centering feature 204A of the first coupling interface 202A can be configured such that it cannot be received in the rotation stop 206B of the second coupling interface 202B. Likewise, the rotation stop 206A of the first coupling interface 202A can be configured such that it cannot be received in the centering feature 204B of the second coupling interface 202B, or at least not while still locking the any degrees of freedom. In some embodiments, the diameter D3 of the rotation stop 206B can be the same or larger than the diameter D2 of the bushing 214 of the centering feature 204B.

As shown, the centering feature 204B and the rotation stop 206B of the second coupling interface 202B can include a gap 243 between the bushings 214, 216 and the first and second recesses 236a, 236b. The gap 243 can allow the bushings 214, 216 to deform and/or flex during coupling 200 to form a unique coupling between the first and second coupling interfaces 202A, 202B precisely and accurately. The gap 243 can also allow for the recesses 236a, 236b and outer surfaces of the bushings 214, 216 to be cleaned more easily.

Figure 7:
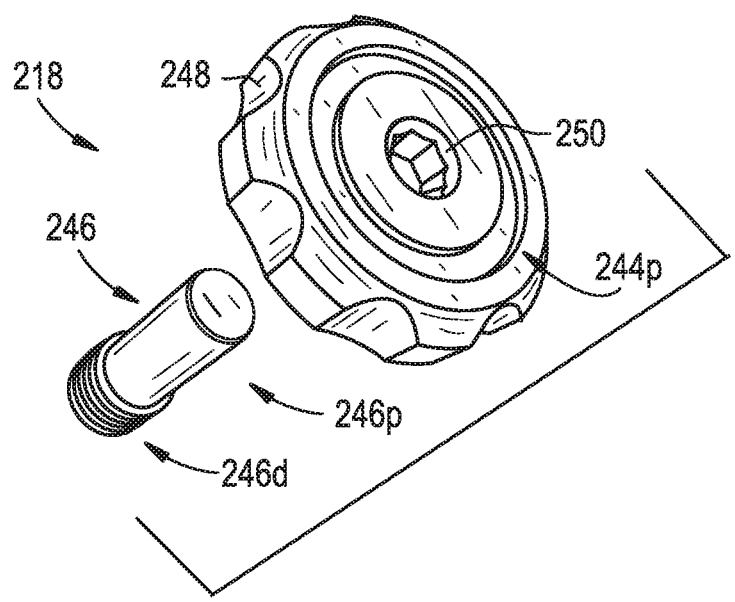
FIG. 7 is an exploded perspective view of a locking element of the coupling of FIG. 2.

FIG. 7 illustrates an exemplary embodiment of the locking element 218 that can be used with the coupling 200. While a screw-type locking element is shown, other locking elements can be used instead or in addition. In some embodiments, the locking element can be friction between the counterpart centering features and/or counterpart rotation stops. In other words, Z direction separation of the coupling interfaces 202A, 202B can be blocked by friction between the mated components, without necessarily requiring a separate screw or other locking component.

The locking element 218 can extend through a portion of the coupling 200 to secure the first and second coupling interfaces 202A, 202B to one another. For example, the locking element 218 can extend through the centering features 204A, 204B to help maintain a position of the first and second interfaces 202A, 202B during coupling. In some embodiments, the locking element 218 can extend through the rotation stops 206A, 206B or the reference planes 208A, 208B to maintain engagement between the first and second coupling interfaces 202A, 202B.

The locking element 218 can include a handle 244 and a post 246. The handle 244 can be shaped like a circular knob, as shown, or can have various other shapes, such as linear, oval, oblong, square, rectangular, triangular, and so forth. The handle 244 can include one or more gripping surfaces 248 thereon. The gripping surfaces 248 can be located on a perimeter of the handle 244. The gripping surfaces 248 can allow a user to rotate the locking element 218 to manipulate its orientation. In the illustrated embodiment, rotation of the handle 244 in a first direction, e.g., clockwise, can distally translate the locking element 218 to secure engagement between the first and second coupling interfaces 202A, 202B, whereas rotation of the handle 244 in a second, opposite direction, e.g. counterclockwise, can proximally translate the locking element 218 to loosen the engagement between the first and second coupling interfaces 202A, 202B. In some embodiments, the locking element 218 can be configured to mate with a modular handle, powered driver, manual, electric, hydraulic, or pneumatic drill or driver tool, or another tool to dispose the locking element 218 within the coupling 200. A distal surface 244d of the handle 244 can be configured to abut the second coupling interface 202B during coupling.

It will be appreciated that although the handle 244 and post 246 are shown as separate components, in some embodiments, the handle and post can be integrally formed. While a screw-type locking element 218 is shown, in other arrangements the locking element can be a clamp, a dovetail connection, a band, or any of a variety of other devices for attaching two objects.

The handle 244 can include an opening 250 formed therein. The opening 250 can extend along the axis A1 from a proximal surface of the handle 244p to the distal surface 244d of the handle 244. The opening 250 can be configured to receive the post 246 therethrough. The post 246 can extend through a portion of the opening 250 or pass entirely through the opening 250. The post 246 can include two separate components, though, in some embodiments, the post can be a single, integrated piece. The proximal portion of the opening 250 can define a drive interface for receiving a driver tool therein.

As shown, the post 246 can include a non-threaded proximal portion 246p and a distal threaded portion 246d. The threaded portion 246d can engage with the threaded surface 224t of the centering feature 204A to secure the first and second coupling interfaces 202A, 202B. The length of the post 246 over which the threads extend and/or the length of the bore 224 that is unthreaded can be selected to achieve various functions during coupling. For example, the lengths can be selected such that the threads engage before the second coupling interface 202B is fully seated on the first coupling interface 202A. In such arrangements, the threads can provide mechanical advantage to help draw the coupling interfaces 202A, 202B together during mating and to urge the coupling interfaces apart during decoupling. As another example, the lengths can be selected such that the threads do not engage before the second coupling interface 202B is fully seated on the first coupling interface 202A. In such arrangements, the need to tighten the locking element 218 prior to fully seating the second coupling interface 202B on the first coupling interface 202A can be eliminated. Also, having the coupling interfaces 202A, 202B in aligned position before introducing the locking element 218 therethrough can ensure that the locking element 218 does not secure the coupling 200 in a misaligned orientation when advanced through the centering features 204A, 204B. While a threaded post 246 is shown, it will be appreciated that any of a variety of other mating features can be used instead or in addition, such as bolts, screws, wedges, and the like.

FIGS. 8A-8D illustrate a method of using the coupling 200 to attach a first object to a second object, e.g., a navigation array to an instrument. Except as indicated below and will be readily appreciated by one having ordinary skill in the art, the steps of the described method can be performed in various sequences, and one or more steps can be omitted or added. Additionally, the instruments illustrated in the drawings are merely exemplary and alternative embodiments of the instruments, e.g., different configurations of the first and second coupling interfaces, the locking element, etc., can be used in conjunction with the steps described below. A detailed description of every sequence of steps is omitted here for the sake of brevity.

Figure 8A:
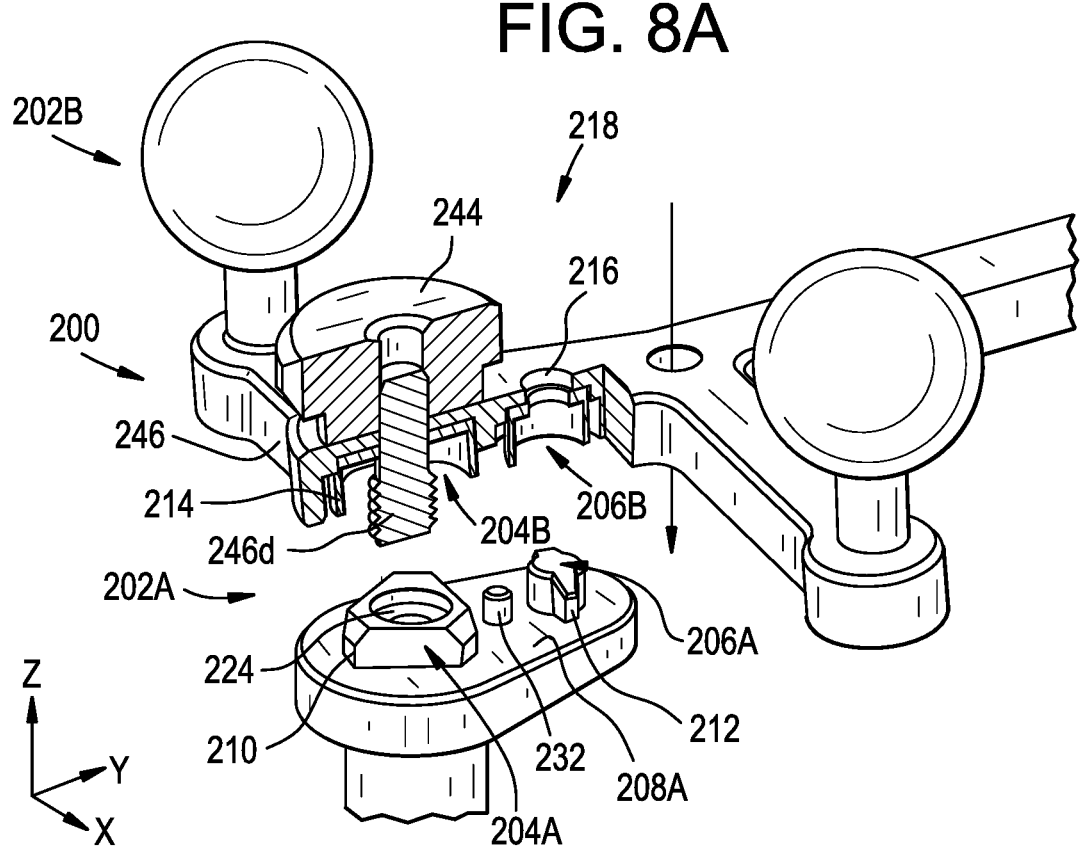
FIG. 8A is a partially-sectioned perspective view of the first and second coupling interfaces of FIG. 2 prior to coupling.
Figure 8B:
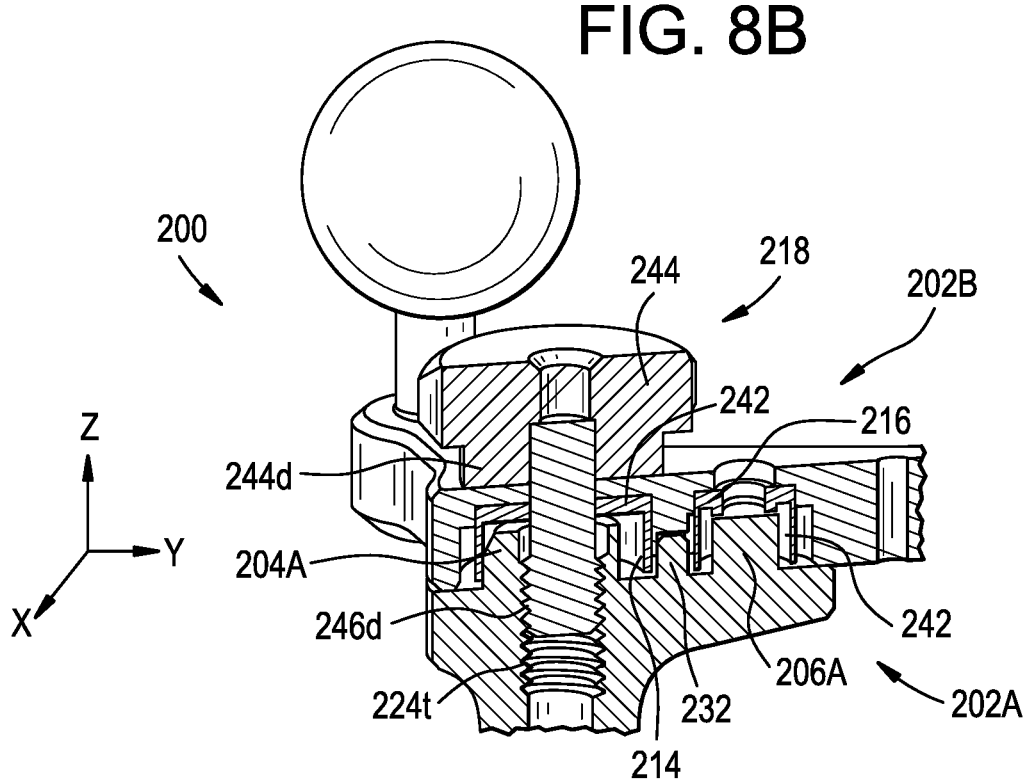
FIG. 8B is a sectional perspective view of the first and second coupling interfaces of FIG. 2 after coupling.

FIG. 8A illustrates attachment of a navigation array and a surgical instrument by engaging the second coupling interface 202B with the first coupling interface 202A. The second coupling interface 202B can be aligned with the first coupling interface 202A such that the centering feature 204B and the rotation stop 206B of the second interface 202B receive the centering feature 204A and the rotation stop 206A of the first interface 202A therethrough, respectively. As shown, the locking element 218 can be retained to the second coupling interface 202B prior to coupling, though, the locking element 218 can also be introduced after the first and second coupling interfaces 202A, 202B are coupled. The threaded portion 246d of the post 246 can extend distally from the second coupling interface 202B and the bushing 214, as shown, though the post 246 can be proximal to the bushing 214 and/or the planar contact surface 208B, or introduced after the reference planes 208A, 208B are engaged with one another, to maintain consistent positioning between the first and second interfaces 202A, 202B and lock all six degrees of freedom of the coupling 200.

Once the centering feature 204A and the rotation stop 206A engage the corresponding centering feature 204B and the rotation stop 206B, the second interface 202B can proceed distally to abut the planar contact surfaces 208A, 208B. In some embodiments, the centering feature 204B and the rotation stop 206B of the second interface 202B translate distally along the lead-in surfaces 222, 228 of the first coupling interface 202A. Distal translation of the second coupling interface 202B relative to the lead-in surfaces 222, 228 can center the coupling interfaces 202A, 202B relative to one another and can prevent damage to the contact surfaces 210, 212 that can be caused by the coupling interfaces 202A, 202B sliding relative to one another.

Once the first and second coupling interfaces 202A, 202B are properly aligned with one another, a force applied to the second interface 202B can complete the coupling. Applying a distal force onto the second coupling interface 202B once the centering feature 204B and the rotation stop 206B of the second coupling interface 202B are adjacent to the contact surfaces 210, 212 can lock the contact surfaces 210, 212 in contact with the bushings 214, 216. The contact surfaces 210, 212 can engage the bushings 214, 216 by an elastic press-fit connection.

The distal force can flex and/or deform the bushings 214, 216 within the first and second recesses 236a, 236b to allow further distal translation of the bushings 214, 216 relative to the centering feature 204A and the rotation stop 206A. Deformation of the bushings 214, 216 can continue until the planar contact surfaces 208A, 208B abut one another. Contact between the planar surfaces 208A, 208B can stabilize the coupling 200 and prevent Z-axis translation of the coupling in a first direction, as well as block rotation of the coupling 200 about the X- and Y-axes. Z-axis translation in a second, opposite direction can be blocked by the locking element 218 or by friction between the counterpart centering features and/or the counterpart rotation stops.

Figure 8C:
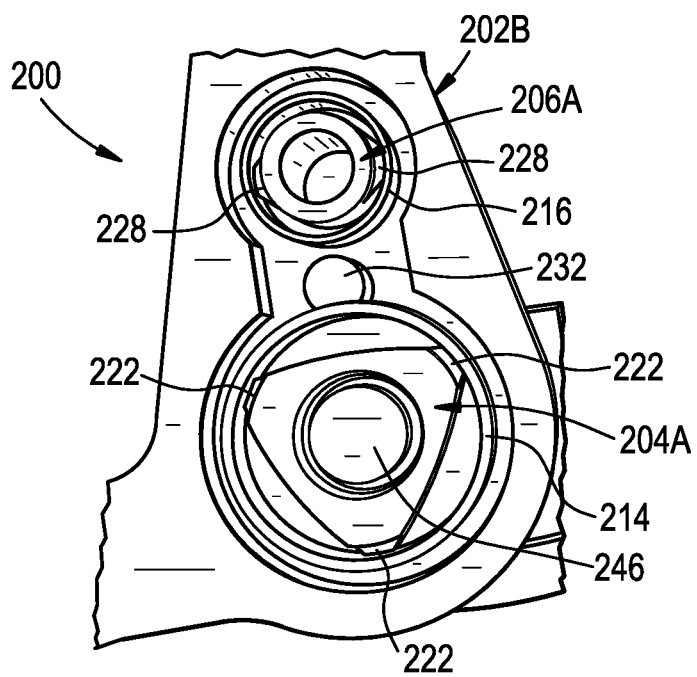
FIG. 8C is a sectional top view of the assembled coupling of FIG. 8B.
Figure 8D:
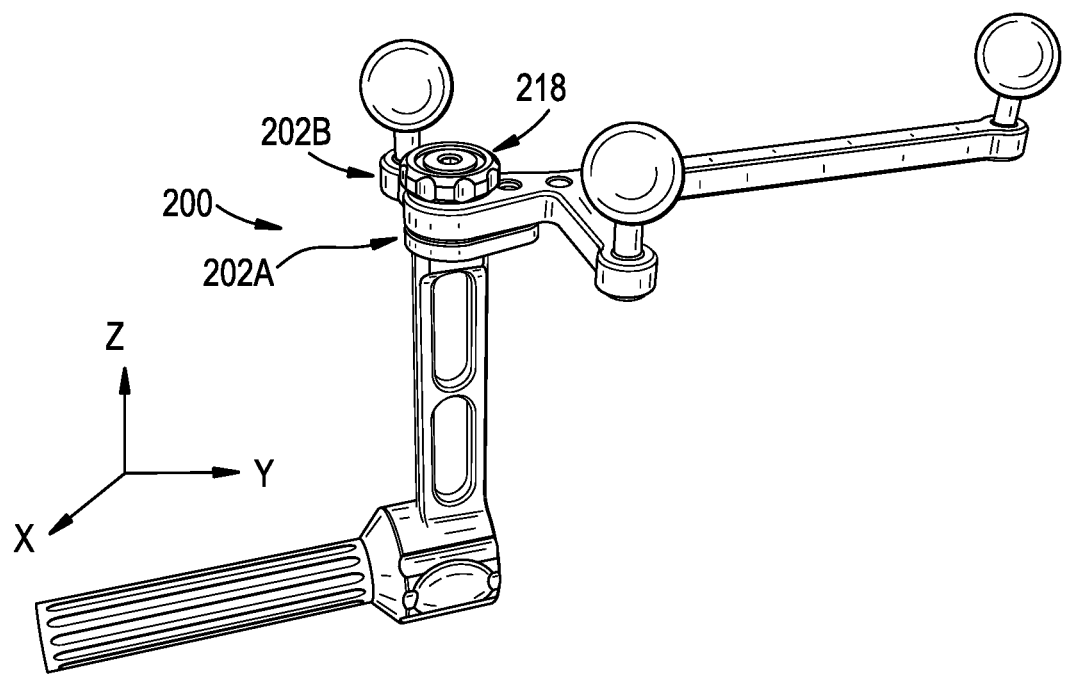
FIG. 8D is a perspective view of the assembled coupling of FIG. 8B.

The bushings 214, 216 can engage the contact surfaces 210, 212 of the centering feature 204A and the rotation stop 206A to couple the first and second coupling interfaces 202A, 202B, as shown in FIG. 8C. Contact between the first bushing 214 and the contact surfaces 210 of the centering feature 204A can block X- and Y-axis translation of the coupling. Contact between the second bushing 216 and the contact surfaces 212 of the rotation stop 206A can block rotation about the Z-axis. The locking element 218 can be tightened as shown in FIG. 8D to prevent Z-axis separation of the coupling interfaces, thereby locking the coupling 200 in all six degrees of freedom and maintaining the coupling interfaces 202A, 202B in contact with one another.

To decouple the navigation array from the instrument, the handle 244 can be rotated in the second direction. As the threaded portion 246d moves proximally through the bore 224, a proximal end of the threaded portion 246d can exit the threaded surface 224t and abut the underside of the second coupling interface 202B while a distal end of the threaded portion 246d remains engaged with the threaded surface 224t. Further rotation of the handle 244 can thus urge the second mating interface 202B away from the first mating interface 202A to facilitate disassembly.

Generally, the first and second coupling interfaces 202A, 202B can be manufactured from a hard metal, such as steel, titanium, and the like to reduce wear and allow reuse of the instruments or objects on which the coupling interfaces are formed. In some embodiments, for example in the case of a single use instrument, one or both of the first and second interfaces 202A, 202B can be manufactured from plastic. While the plastic may be deformed or degraded after use with a metallic counterpart, this can be tolerated in a single use application. For example, the centering feature 204A and the rotation stop 206A can be made from a plastic material, e.g., polystyrene, low-density polyethylene, etc.

The first and second coupling interfaces 202A, 202B can each be manufactured and/or machined from a single orientation of the manufacturing tool. For example, the coupling interfaces 202A, 202B each can be milled from a single side, which can improve manufacturing accuracy as there is no need to flip either coupling interface and/or realign the interfaces during milling. This can minimize manufacturing tolerances and help ensure that the centering features 204A, 204B and the rotation stops 206A, 206B fit snugly within one another to form a coupling 200 that can lock all of the degrees of freedom and ensure consistent positioning. In some embodiments, other openings, e.g., locations on the navigation array that receive fiducial markers therethrough, can also be milled from the same side as the coupling interfaces, which can further ensure consistency in manufacturing.

The coupling 200 can be used with any of a variety of instruments or objects. In some embodiments, one of the coupling interfaces 202A, 202B can include or can be attached to or formed on a navigation array. A position and orientation of the coupling interface with respect to the navigation array 300 can be known, such that the position and orientation of an instrument attached to the array by the coupling 200 can be determined from the position and orientation of the array.

Figure 9A:
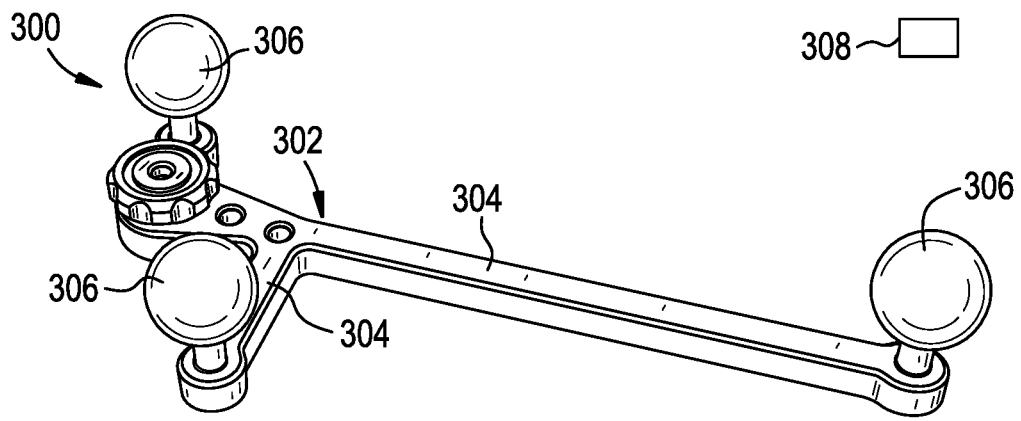
FIG. 9A is a perspective view of a navigation array that can be used with the coupling of FIG. 2.
Figure 9B:
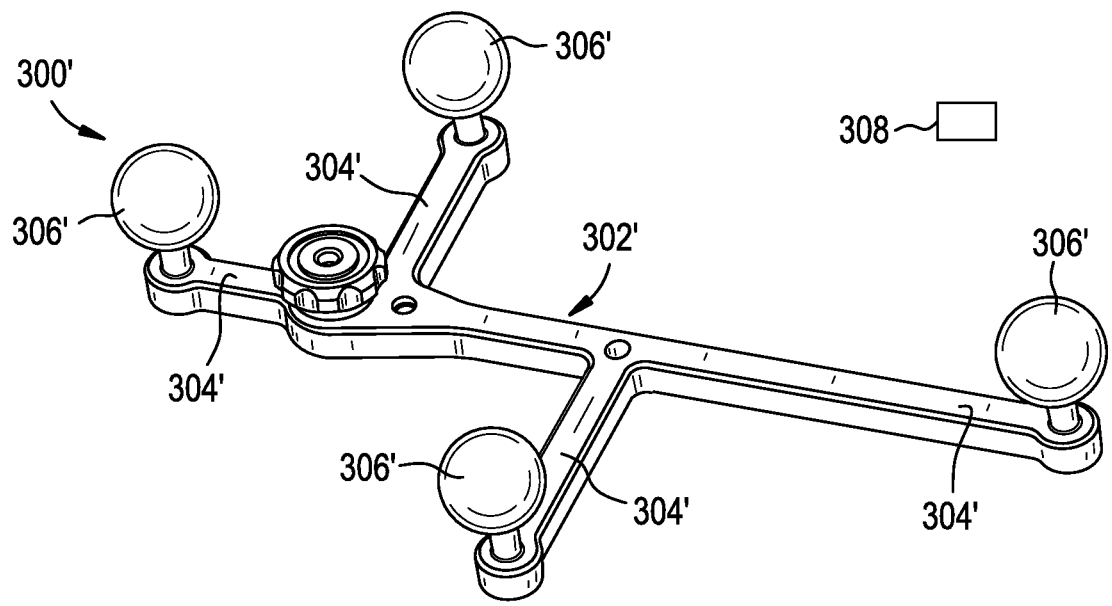
FIG. 9B is a perspective view of another navigation array that can be used with the coupling of FIG. 2.

Exemplary embodiments of navigation arrays are shown in FIGS. 9A-9B. The navigation array 300 can include a frame 302 having the second coupling interface 202B formed thereon, e.g., on a surface thereof, or attached thereto. The frame can include one or more branches 304 extending therefrom, each branch having a sphere-shaped fiducial or other marker 306 attached thereto for use with a navigation system. The fiducials 306 can be arranged in predetermined positions and orientations with respect to one another. The fiducials 306 can be positioned within a field of view of a navigation system 308 and can be identified in images captured by the navigation system. Exemplary fiducials 306 include infrared reflectors, LEDs, and so forth. The navigation array 300 can be or can include an inertial measurement unit (IMU), an accelerometer, a gyroscope, a magnetometer, other sensors, or combinations thereof. The sensors can transmit position and/or orientation information to the navigation system, e.g., to a processing unit of the navigation system.

The navigation array 300 can be detected by the navigation system 308, can communicate with the navigation system 308, or can be otherwise operably coupled to the navigation system 308 to allow the position and/or orientation of an instrument attached thereto by the coupling 200 to be registered with and tracked by the navigation system 308. It will be appreciated that the structure and operation of the navigation array 300 can vary depending on the type of navigation system used. For example, as shown in FIG. 9B, another embodiment of a navigation array 300' having a frame 302' that includes four branches 304', each branch having a sphere-shaped fiducial or other marker 306' attached thereto, can be used with the navigation system 308.

Figure 10A:
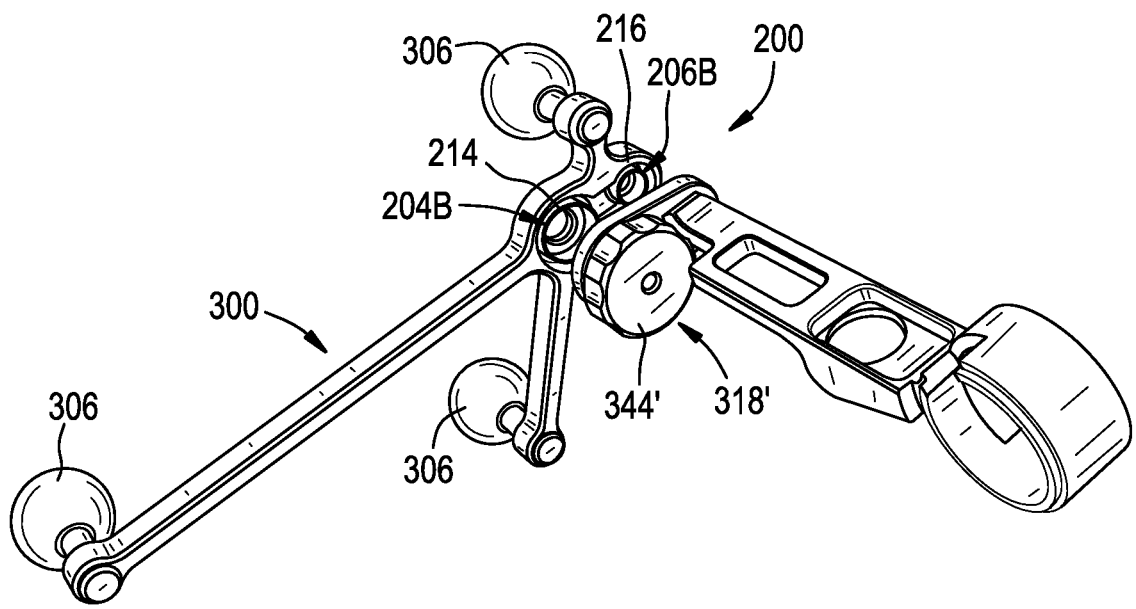
FIG. 10A is a perspective view of another locking element configuration that can be used with the couplings described herein, shown with a coupling configured to attach a navigation array to a surgical instrument.
Figure 10B:
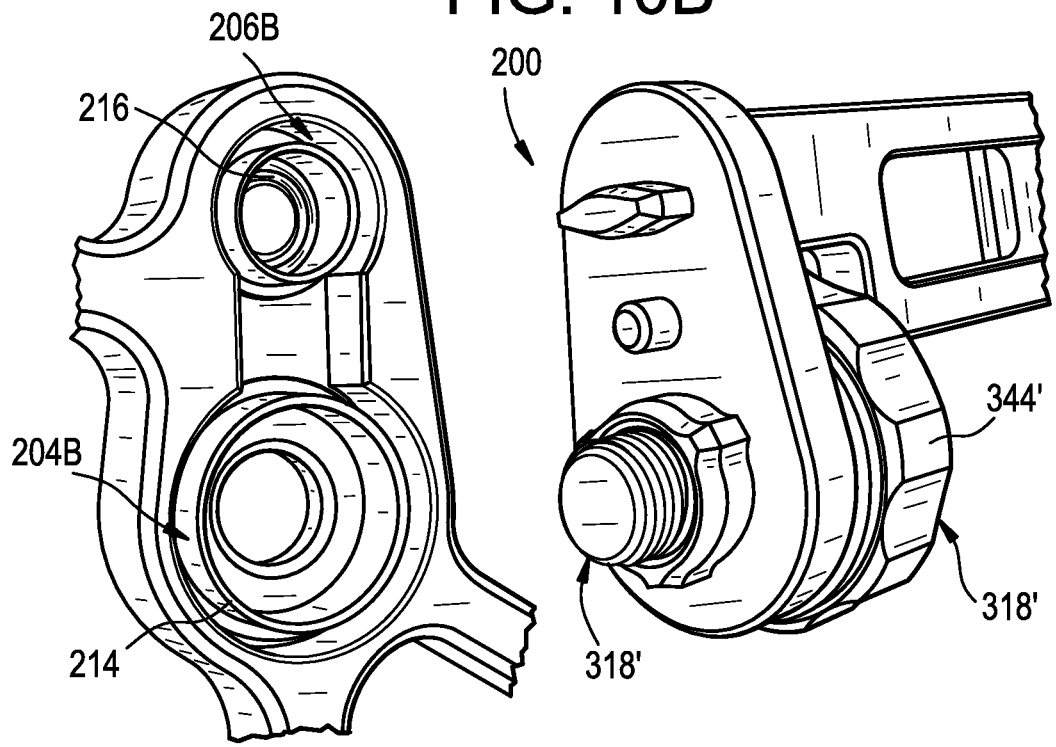
FIG. 10B is a detail perspective view of the locking element and coupling of FIG. 10A.

In the arrays shown in FIGS. 9A-9B, a coupling interface (e.g., the first or second coupling interfaces described above) can be disposed on a lower surface or lower side of the array. A locking element can be inserted through the array from an upper side to the lower side for attachment to an instrument that is to be mated to the array. In other arrangements, the locking element can be inserted through the instrument first and then into the array. For example, as shown in FIGS. 10A-10B, a locking element 318' can be inserted first through an instrument side of the coupling and then threaded into or otherwise attached to the array side of the coupling. Inserting the locking element 318' from the instrument side of the coupling 200 can prevent the handle or knob 344' of the locking element from interfering with the fiducials 306 of the navigation array 300. The locking element 318' can be threaded into one or more of the centering features of the coupling, one or more of the rotation stops of the coupling, or a location other than the centering features or rotation stops. The locking element 318' can be threaded into a bushing of the coupling, e.g., one of the first and second bushings 214, 216.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

The devices disclosed herein can be constructed from any of a variety of known materials. Exemplary materials include those which are suitable for use in surgical applications, including metals such as stainless steel, titanium, nickel, cobalt-chromium, or alloys and combinations thereof, polymers such as PEEK, ceramics, carbon fiber, and so forth. The various components of the devices disclosed herein can be rigid or flexible. One or more components or portions of the device can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The devices and methods disclosed herein can be used in minimally-invasive surgery and/or open surgery. While the devices and methods disclosed herein are generally described in the context of navigated surgery on a human patient, it will be appreciated that the methods and devices disclosed herein can be used in any type of surgery on a human or animal subject, in non-surgical applications, on non-living objects, and so forth.

Although specific embodiments are described above, it should be understood that numerous changes may be made within the spirit and scope of the concepts described.

The invention claimed is:

1. A coupling for attaching first and second objects, comprising:
    a first coupling interface associated with the first object, the first coupling interface having a first reference plane, a first centering feature, and a first rotation stop;
    a second coupling interface associated with the second object, the second coupling interface having a second reference plane, a second centering feature, and a second rotation stop; and
    a locking screw configured to maintain the first and second coupling interfaces in a mated relationship,
    wherein the first and second coupling interfaces are adapted to mate with one another such that the first reference plane contacts the second reference plane, the first centering feature contacts the second centering feature, and the first rotation stop contacts the second rotation stop,
    wherein the first centering feature comprises a centering protrusion and the second centering feature comprises a centering recess, and
    wherein the centering protrusion has a triangular transverse cross-section.

2. The coupling of claim 1, wherein the first centering feature makes cylindrical three point contact with the second centering feature; and wherein the first rotation stop makes cylindrical two point contact with the second rotation stop.

3. The coupling of claim 1, wherein the first and second reference planes, when mated, lie in XY planes of a Cartesian system having an X-axis, a Y-axis, and a Z-axis.

4. The coupling of claim 3, wherein the first and second centering features mate to block X-axis translation and Y-axis translation between the first and second objects.

5. The coupling of claim 3, wherein the first and second rotation stops mate to block Z-axis rotation between the first and second objects.

6. The coupling of claim 3, wherein the first and second reference planes mate to block Z-axis translation in a first direction, X-axis rotation, and Y-axis rotation between the first and second objects.

7. The coupling of claim 6, further comprising a locking element that blocks Z-axis translation in a second direction between the first and second objects.

8. The coupling of claim 7, wherein the locking element comprises at least one of: (i) friction between the centering features, (ii) friction between the rotation stops, (iii) a screw, and (iv) a clamp.

9. The coupling of claim 1, wherein the centering protrusion is press-fit into the centering recess.

10. The coupling of claim 1, wherein the centering recess is configured to elastically deform upon insertion and removal of the centering protrusion therefrom.

11. The coupling of claim 1, wherein the centering protrusion includes three cylindrical outer contact surfaces configured to contact a cylindrical inner sidewall of the centering recess.

12. The coupling of claim 11, wherein the centering protrusion includes oblique lead-in surfaces disposed adjacent to the contact surfaces.

13. The coupling of claim 1, wherein the centering recess is recessed relative to the second reference plane.

14. The coupling of claim 1, wherein the first rotation stop comprises a rotation stop protrusion and the second rotation stop comprises a rotation stop recess.

15. The coupling of claim 14, wherein the rotation stop protrusion is press-fit into the rotation stop recess.

16. The coupling of claim 14, wherein the rotation stop recess is configured to elastically deform upon insertion and removal of the rotation stop protrusion therefrom.

17. The coupling of claim 14, wherein the rotation stop protrusion includes two cylindrical outer contact surfaces configured to contact a cylindrical inner sidewall of the rotation stop recess.

18. The coupling of claim 17, wherein the rotation stop protrusion includes oblique lead-in surfaces disposed adjacent to the contact surfaces.

19. The coupling of claim 14, wherein the rotation stop protrusion includes two contact surfaces disposed along an arc centered on the first centering feature.

20. The coupling of claim 14, wherein the rotation stop protrusion has a circular transverse cross-section with first and second lateral wings extending therefrom.

21. The coupling of claim 14, wherein the rotation stop recess is recessed relative to the second reference plane.

22. The coupling of claim 1, wherein the one of the first and second objects is a surgical navigation array and the other of the first and second objects is a surgical instrument.

23. The coupling of claim 1, further comprising an alignment pin configured to prevent mating of the first and second coupling interfaces when the first and second coupling interfaces are not in a pre-determined alignment with one another.

24. The coupling of claim 1, wherein the locking screw extends through the first and second centering features.

* * * * *